(12) United States Patent
Kauschke et al.

(10) Patent No.: US 7,152,664 B2
(45) Date of Patent: Dec. 26, 2006

(54) INCUBATION AND STORAGE DEVICE, IN PARTICULAR FOR SPECIMENS OF ORGANIC MATERIAL

(75) Inventors: Marion Kauschke, Aschaffenburg (DE); Dieter Bidlingmaier, Bruchköbel (DE)

(73) Assignee: Kendro Laboratory Products, Hanau (DE)

( * ) Notice: Subject to any disclaimer, the term of this patent is extended or adjusted under 35 U.S.C. 154(b) by 125 days.

(21) Appl. No.: 10/274,113

(22) Filed: Oct. 21, 2002

(65) Prior Publication Data

US 2003/0085218 A1 May 8, 2003

(30) Foreign Application Priority Data

Nov. 1, 2001 (DE) ................................ 101 54 663

(51) Int. Cl.
 *F25B 29/00* (2006.01)
 *A01K 41/00* (2006.01)

(52) U.S. Cl. .................. 165/48.1; 165/61; 119/311; 119/312; 119/315

(58) Field of Classification Search .............. 165/47, 165/48.1, 53, 54, 58, 61, 65, 168; 435/809, 435/303.1, 286.6; 422/298, 104; 119/311, 119/312, 315, 316

See application file for complete search history.

(56) References Cited

U.S. PATENT DOCUMENTS

| | | | | |
|---|---|---|---|---|
| 1,902,625 A | * | 3/1933 | Dunham | 422/298 |
| 2,124,250 A | | 7/1938 | Hoag | 34/21 |
| 4,336,329 A | * | 6/1982 | Hesse et al. | 422/298 |
| 4,701,415 A | * | 10/1987 | Dutton et al. | 435/286.6 |
| 5,542,375 A | * | 8/1996 | Voren | 119/312 |
| 5,773,287 A | * | 6/1998 | Binder | 435/303.1 |
| 6,280,781 B1 | * | 8/2001 | Lande | 426/34 |
| 6,333,004 B1 | * | 12/2001 | Sheldon | 422/122 |
| 6,503,751 B1 | * | 1/2003 | Hugh | 422/104 |

FOREIGN PATENT DOCUMENTS

| | | |
|---|---|---|
| DE | 19925154 | 5/2001 |
| DE | 19952330 | 5/2001 |
| EP | 0967268 | 12/1999 |
| EP | 1148120 | 10/2001 |
| WO | WO 97 21834 | 6/1997 |

OTHER PUBLICATIONS

European Search Report dated Feb. 26, 2003.

* cited by examiner

*Primary Examiner*—Ljiljana Ciric
(74) *Attorney, Agent, or Firm*—Baker & Hostetler LLP

(57) ABSTRACT

An incubation and storage device, in particular for specimens of organic material, is provided. Specifically, boundary surfaces of the inner space of the incubation and storage device are thermally connected to heat transfer elements that are attached on the outside of the device. The heat transfer elements have a liquid heat carrier circulating through them, where the heating and/or cooling of the inner space takes indirectly via the liquid heat carrier. Here a heater for heating and an evaporator for cooling the heat carrier are provided. The heat transfer elements can for example, be box shaped or designed as tubular coils. Through the use of a liquid heat carrier, the necessary temperature constancy inside the device is achieved.

15 Claims, 2 Drawing Sheets

INCUBATION AND STORAGE DEVICE, IN PARTICULAR FOR SPECIMENS OF ORGANIC MATERIAL

FIELD OF THE INVENTION

The invention concerns an incubation and storage device, in particular for specimens of organic material.

BACKGROUND OF THE INVENTION

Devices of the said kind are used in biology and medicine, for example, to store organic materials under specific external conditions.

Such devices for the cultivation and storage of microorganisms that can greatly accelerate their growth under special living conditions are widely found. In general, the temperature in these devices is, as an important growth parameter, kept constant at a certain level for a long time. However, there are also instances in which temperatures determined according to a preset temperature program are reached at certain times and kept constant for a certain time. These devices are frequently outfitted with heating devices and cooling units both for heating and cooling operation.

Temperature-controlled incubation devices or storage devices for storage of tissues are used in medicine.

It is very important for hygienic reasons that it be very easy to clean these devices. This is necessary in particular to prevent transmission of germs and undesired infections.

Various basic forms of incubation and storage devices are known in the prior art.

One distinguishes among the following systems:

1. Direct Evaporators for Cooling Agents and Electrical Heating Elements.

Here the electrical heating elements are brought to the inner container of the incubation device from outside or in rare cases are arranged in the inner space. Cooling takes place via the cooling agent evaporator, which is arranged directly in the internal space, for example. Alternatively, a part of the internal air is brought to the evaporator via a bypass and cooled before the cooled air is returned to the inner space of the incubation device.

A disadvantage of this known solution is that the two separate systems for heating and cooling the incubation device are very costly and difficult to control with regard to maintaining a preset temperature. The overlapping of cooling and heating is frequently very high because of the inertia of the individual systems so that tradeoffs involving the temperature constancy have to be made or costly control systems have to be installed. In particular, it is difficult to match the heating and cooling systems to each other so that temperature constancy with low deviation of temperature around a set point is achieved.

2. Indirect Cooling and Electrical Heating Elements

One such system is disclosed in DE 873892. In this case tubular heating elements in supports are arranged in the inner space and, according to one embodiment of the object of said invention, they can also be in part replaced by cooling tubes. Combined cooling and heating of the inner space is enabled through this.

Again, a disadvantage of this prior art is the costly control system in order to match the separate systems for heating and cooling the inner space of the incubation device to each other. Moreover, the supports, in which the heating elements or the cooling liquid is/are situated, are arranged in the inner space, which has a highly adverse effect on the cleaning capabilities when used in hygienically demanding applications in biology and medicine.

3. Water Jackets

With this system water is used as a heat carrier and circulates in a so-called "water jacket." The water jacket in this case is arranged as a second container around the inner container. In this way the temperature constancy is in fact very good, but the system has extraordinarily high inertia. Temperature programs with short phases of different temperatures practically cannot be realized with this system. Moreover, there is also the disadvantage that this system cannot easily be cooled, since an evaporator will freeze up within a short time. For this reason these systems are suitable only for temperatures that are above room temperature and that can be obtained without a cooling system.

Another disadvantage of direct heating that may be pointed out is the fact that the electrical heating elements that are used produce a very high temperature with very low surface area, so that the heat is released to the air in the inner space of the incubation device through radiation and convection. However, since a temperature of only 37° C., for example, is required, flows of different temperature arise rather than the desired average value being established. Thus it is difficult not only from the standpoint of control technology but also flow technology to distribute the temperature uniformly in the inner space.

SUMMARY OF THE INVENTION

It is a task of the invention to design an incubation and storage device that is suitable for temperature control of samples of organic material and, moreover, is easy to clean in the inner space. Moreover, constant maintenance of temperature in the inner space is to be ensured.

In accordance with the invention, the task is solved by the fact that the incubation and storage device is heated and cooled indirectly by a liquid heat carrier. For this the boundary surfaces of the inner space of the incubation and storage device are thermally combined with heat transfer elements attached on the outside, where the heat transfer elements in turn have a liquid heat carrier circulating in them.

Means for cooling and heating the heat carrier are also provided in accordance with the invention.

The required temperature constancy is advantageously easily achieved inside the device through the use of a heat carrier.

The combined indirect cooling and heating shows up advantageously in particular for inner space temperatures close to ambient temperature. Dynamic temperature control of the inner space is possible via this system of heating and cooling connected to a heat carrier circulation loop, through which a change of temperature due to changed input power can be avoided.

BRIEF DESCRIPTION OF THE DRAWINGS

Other details, characteristics and advantages of the invention result from the following description of embodiment examples with reference to the pertinent drawing. Here.

DETAILED DESCRIPTION

Figure 1:
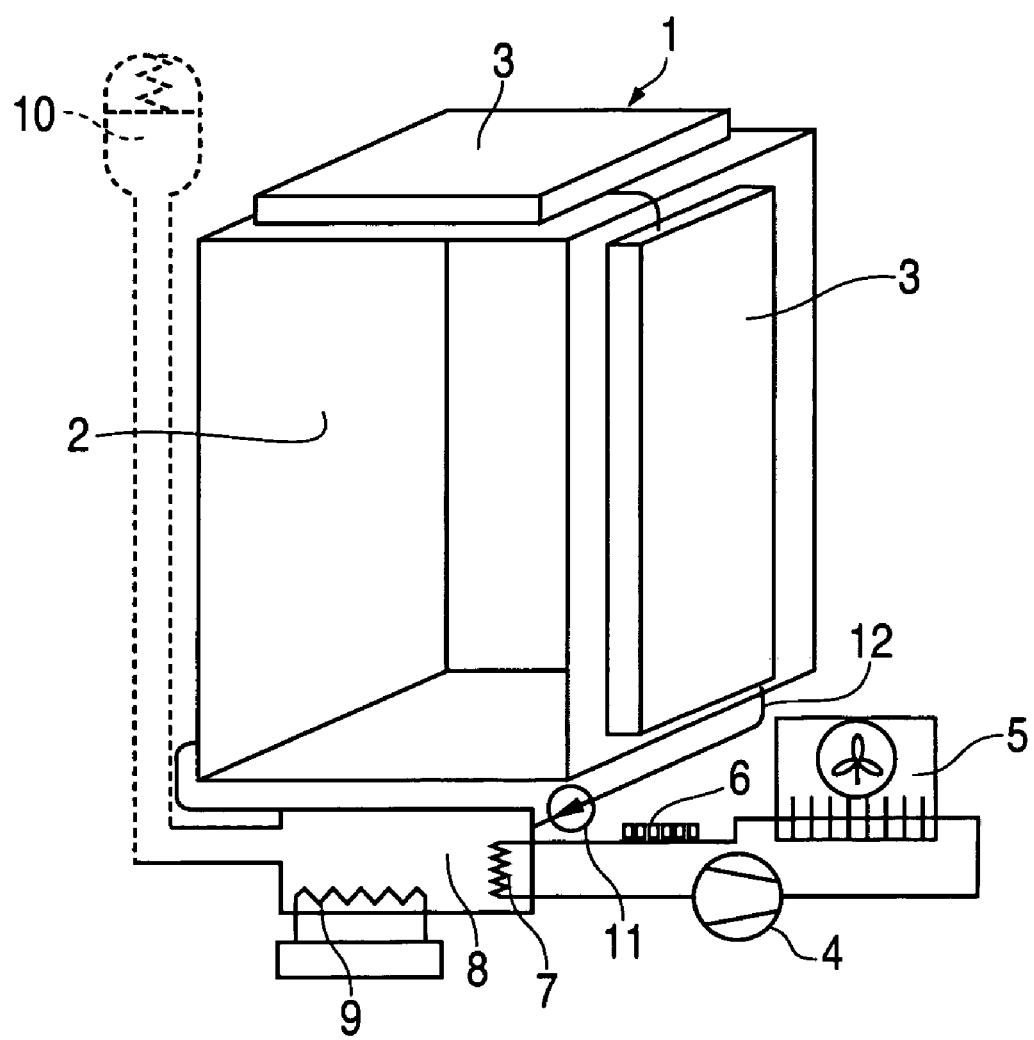
FIG. 1: perspective drawing of an incubation and storage device.

In FIG. 1 an embodiment of an incubation and storage device in accordance with the invention is shown in perspective view. The inner space 2 is formed by inner boundary surfaces, on which heat transfer elements 3 are attached from outside.

The heat transfer elements 3 are thermally combined with the boundary surfaces of inner space 2 or form a part of the boundary surfaces.

A liquid heat carrier flows in circulation through the heat transfer elements 3 and in each case according to the temperature, absorbs heat from the inner space 2 of the incubation and storage device 1 or gives up heat to the inner space 2. The liquid heat carrier is preferably pumped in circulation by means of a pump 11.

The heat transfer elements 3 are, in accordance with the presented preferred embodiment of the invention, shaped as boxes. These box-shaped heat transfer elements 3 are bonded to the boundary surfaces of the inner space 2 by pipe connections 12. The heat transfer liquid is heated via a heat transfer means 9 of a heater (not shown), or is cooled through the heat transfer means/evaporator 7 of a cooling unit.

The cooling unit additionally has a compressor 4, in which the vapor cooling agent is compressed. In condenser 5, shown as an air condenser in the embodiment example, the condensing agent is condensed, depressurized in expansion element 6 and finally goes to the evaporator 7, where it evaporates while absorbing heat from the heat transfer agent. The cooling agent vapor is drawn in by compressor 4, thus closing the cooling agent cycle.

The heat carrier agent is alternatively advantageously completed by an equalizing vessel 10, which balances the volume variations of the heat carrier caused by a change of temperature. The two heat transfer means 7 and 9 for cooling and heating the heat carrier are arranged in a heat carrier reservoir 8 in accordance with the preferred embodiment. An advantageous dynamic for regulation of the heat carrier circulation results from this.

Figure 2:
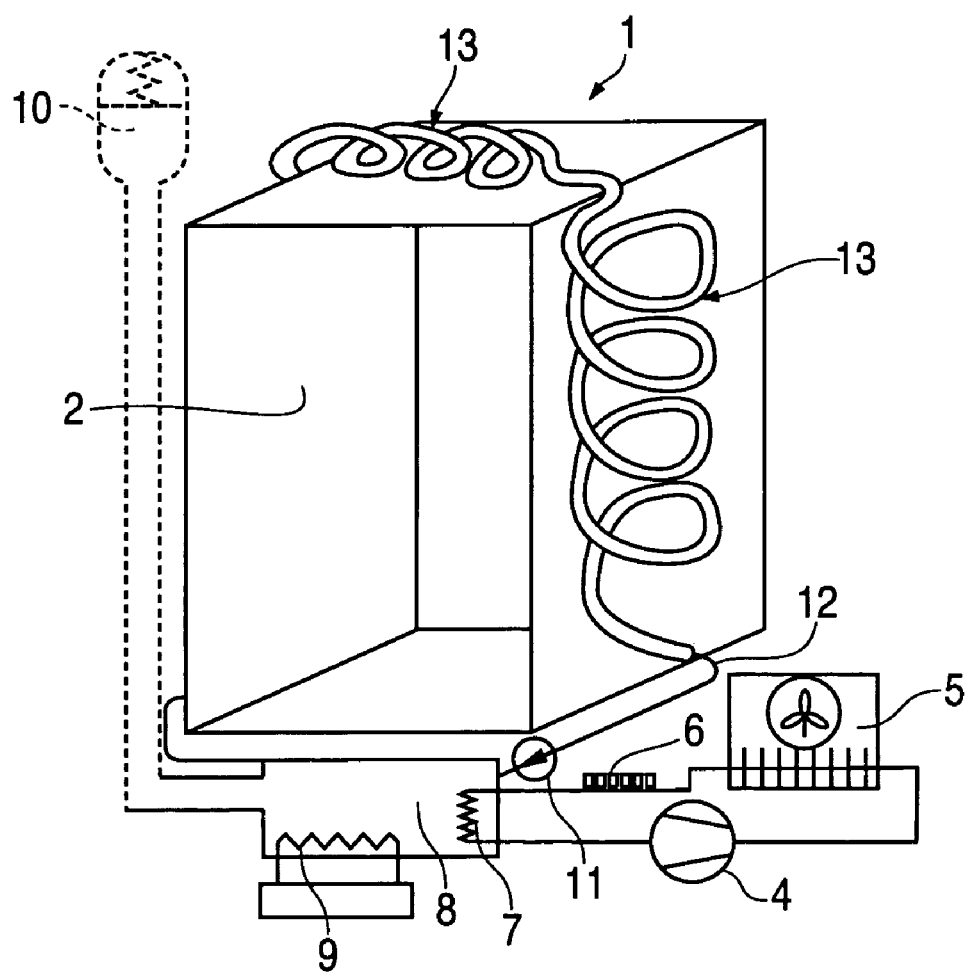
FIG. 2: perspective drawing of a second embodiment of an incubation and storage device.

Referring to FIG. 2, the heat transfer elements are arranged as tubular hoses 13 according to another embodiment of the invention. These run the boundary surfaces of the inner space 2 and are thermally combined with it.

It is also advantageous for temperature control of the incubation and storage device to use an external thermostat with cooling and heating functions or an internal heating appliance and optionally an external cooling appliance. For this the external components are outfitted with the necessary connections and a container for holding the heat carrier and a pump. In addition, the external components are provided with a suitable temperature regulation.

In the case of an incubation and storage device with an external cooling plant the heat carrier system is advantageously designed as an open or expandable system. In this way the cooling capacity reserves of the cooling plant can be used for other purposes via the connections provided in the heat carrier system.

In order to prevent condensation of atmospheric humidity on the viewing windows of the incubation and storage device the transparent surfaces, for example, glass panes, are designed to be heatable.

The heating of the heat carrier of the incubation and storage device is advantageously carried out by means of resistance heating.

R134a, propane, butane or carbon dioxide is advantageously used as coolant for the refrigeration plant.

A mixture of water and glycol is preferably used as heat carrier for the incubation and storage device in accordance with the invention.

LEGEND TO DRAWING

1 Incubation and storage device
2 Inner space
3 Heat transfer element
4 Compressor
5 Condenser
6 Expansion element
7 Heat transfer means/evaporator
8 Heat carrier reservoir
9 Heat transfer means of heater
10 Compensation vessel of heat carrier system
11 Pump
12 Pipe connection

The invention claimed is:

1. An incubation and storage device, comprising:
   a heat transfer element disposed on an outside surface of the incubation and storage device;
   a boundary surface of an inner space of the incubation and storage device thermally connected to the heat transfer element;
   a heater and an evaporator arranged in a heat carrier reservoir spaced apart from the incubation and storage device;
   a liquid heat carrier that is configured to circulate through the heat transfer element; and
   an equalization vessel configured for the circulation of the liquid heat carrier, wherein heating and/or cooling of the inner space takes place directly via the liquid heat carrier.

2. The incubation and storage device as in claim 1, wherein the heat transfer element is shaped as a box.

3. The incubation and storage device as in claim 2, wherein the heat transfer element further comprises a plurality of heat transfer elements.

4. The incubation and storage device as in claim 1, wherein the heat transfer element is shaped as a tube coil.

5. The incubation and storage device as in claim 4, wherein the heat transfer element further comprises a plurality of tube coils.

6. The incubation and storage device as in claim 1, wherein the heat transfer element is connected to a pump by a pipe connection in communication with a heater and an evaporator.

7. The incubation and storage device as in claim 1, wherein resistance heating is provided to heat the liquid heat carrier.

8. The incubation and storage device as in claim 1, further comprising a coolant to cool the liquid heat carrier.

9. The incubation and storage device as in claim 1, wherein the heat transfer element is bonded to the outside surface of the incubation and storage device.

10. An incubation and storage device, comprising:
    a heat carrier reservoir comprising a heating unit and a cooling unit, wherein the heat carrier reservoir is spaced apart from the incubation and storage device;
    the cooling unit comprising an evaporator, a compressor, a condenser and an expansion element;
    the heat carrier reservoir, connected to a heat transfer element through a pipe;
    the heat transfer element bonded to a housing; and
    a liquid heat carrier disposed to circulate between the heat transfer element and the heat carrier reservoir through the pipe and wherein the liquid heat carrier is heated by the heater or cooled by the cooling unit.

11. The incubation and storage device of claim 10, wherein the liquid heat carrier circulates through the use of a pump.

12. The incubation and storage device of claim 10, wherein the heat transfer element has a box-like shape.

13. The incubation and storage device of claim 10, wherein the heat transfer element is tubular in shape.

14. The incubation and storage device of claim 10, wherein the heat carrier reservoir is coupled to an equalizing vessel.

15. The incubation and storage device of claim 10, wherein the liquid heat carrier is a mixture of water and glycol.

* * * * *